United States Patent
Giladi et al.

(10) Patent No.: US 11,554,262 B2
(45) Date of Patent: Jan. 17, 2023

(54) DETERMINING A FREQUENCY FOR TTFIELDS TREATMENT BASED ON AN ELECTRICAL CHARACTERISTIC OF TARGETED CANCER CELLS

(71) Applicant: Novocure GmbH, Root (CH)

(72) Inventors: Moshe Giladi, Moshav Herut (IL); Einav Zeevi, Zichron Yaakov (IL); Cornelia Wenger, Ericeira (PT); Zeev Bomzon, Kiryat Tivon (IL)

(73) Assignee: Novocure GmbH, Root (CH)

(*) Notice: Subject to any disclaimer, the term of this patent is extended or adjusted under 35 U.S.C. 154(b) by 379 days.

(21) Appl. No.: 16/800,737

(22) Filed: Feb. 25, 2020

(65) Prior Publication Data

US 2020/0269042 A1    Aug. 27, 2020

Related U.S. Application Data

(60) Provisional application No. 62/810,823, filed on Feb. 26, 2019.

(51) Int. Cl.
*A61N 1/36* (2006.01)
*G01N 27/22* (2006.01)
(Continued)

(52) U.S. Cl.
CPC .......... *A61N 1/36002* (2017.08); *A61B 5/053* (2013.01); *A61N 1/40* (2013.01);
(Continued)

(58) Field of Classification Search
CPC ........ A61N 1/36002; A61N 1/40; A61N 1/08; G01N 27/221; G01N 27/447; G01N 33/4833; G01N 33/48728; A61B 5/053
See application file for complete search history.

(56) References Cited

U.S. PATENT DOCUMENTS 6,868,289 B2    3/2005    Palti
7,016,725 B2    3/2006    Palti
(Continued)

FOREIGN PATENT DOCUMENTS

WO    2018160751 A1    9/2018

OTHER PUBLICATIONS

International Search Report and Written Opinion issued in application No. PCT/IB2020/051613 dated May 26, 2020.

*Primary Examiner* — Amy He
(74) *Attorney, Agent, or Firm* — Potomac Law Group, PLLC (57) ABSTRACT

Cancer treatment using TTFields (Tumor Treating Fields) can be customized to each individual subject by obtaining cancer cells from the subject, determining an electrical characteristic (e.g., dielectrophoretic forces, cell membrane capacitance, etc.) of the cancer cells, determining a frequency for the TTFields based on the determined electrical characteristic, and treating the cancer by applying TTFields to the subject at the determined frequency. In addition, cancer treatment can be planned for each individual subject by obtaining cancer cells from the subject, determining an electrical characteristic of the cancer cells, predicting whether TTFields would be effective to treat the cancer based on the determined electrical characteristic, and treating the subject by applying TTFields if the prediction indicates that TTFields would be effective.

12 Claims, 6 Drawing Sheets

(51) Int. Cl.
  *G01N 27/447* (2006.01)
  *G01N 33/483* (2006.01)
  *G01N 33/487* (2006.01)
  *A61B 5/053* (2021.01)
  *A61N 1/40* (2006.01)

(52) U.S. Cl.
  CPC ......... *G01N 27/221* (2013.01); *G01N 27/447* (2013.01); *G01N 33/4833* (2013.01); *G01N 33/48728* (2013.01)

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2006/0167499 A1 | 7/2006 | Palti |
| 2007/0225766 A1 | 9/2007 | Palti |
| 2007/0239213 A1 | 10/2007 | Palti |
| 2008/0287944 A1 | 11/2008 | Pearson et al. |
| 2009/0076366 A1 | 3/2009 | Palti |
| 2012/0283726 A1 | 11/2012 | Palti |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0206755 A1 * | 7/2018 | Gregory .................. A61B 5/72 |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |

* cited by examiner

DETERMINING A FREQUENCY FOR TTFIELDS TREATMENT BASED ON AN ELECTRICAL CHARACTERISTIC OF TARGETED CANCER CELLS

CROSS REFERENCE TO RELATED APPLICATIONS

This Application claims the benefit of U.S. Provisional Application 62/810,823, filed Feb. 26, 2019, which is incorporated herein by reference in its entirety.

BACKGROUND

Tumor Treating Fields (TTFields) are an effective antineoplastic treatment modality delivered via application of low intensity (e.g., 1-5 V/cm), intermediate frequency (e.g., 100-300 kHz), alternating electric fields. TTFields therapy has received FDA approval for treating Glioblastoma Multiforme brain tumors and appears to be very promising for many other types of tumors. TTFields therapy is delivered using a wearable and portable device (Optune™). The delivery system includes four adhesive, non-invasive, insulated "transducer arrays", an electric field generator, rechargeable batteries, and a carrying case. The transducer arrays are applied to the skin in the vicinity of the tumor and are connected to the field generator.

In the preclinical setting, TTFields can be applied in vitro using the Inovitro™ system by means of perpendicular pairs of electrodes insulated by a high dielectric constant ceramic. Inovitro™ (TTFields lab bench system) is comprised of a TTFields generator and base plate containing 8 ceramic dishes per plate.

SUMMARY OF THE INVENTION

One aspect of the invention is directed to a first method of treating cancer in a subject having a cancerous tissue. The first method comprises obtaining a sample of the cancerous tissue from the subject, the sample having at least one cancer cell; determining an electrical characteristic of the at least one cancer cell; determining a frequency of alternating electric fields to apply to the subject in order to treat the cancer based on the determined electrical characteristic; and treating the cancer by applying an alternating electric field to the subject at the determined frequency of alternating electric fields.

In some instances of the first method, the determining of the electrical characteristic comprises measuring dielectrophoretic forces of the at least one cancer cell at each of a plurality of frequencies below 35 kHz. In some instances of the first method, the determining of the frequency comprises choosing a frequency that is effective in treating reference cancer cells that have a known electrical characteristic, wherein the known electrical characteristic matches the determined electrical characteristic. In some instances of the first method, the determining of the electrical characteristic comprises determining cell membrane capacitance.

Another aspect of the invention is directed to a second method of treating cancer in a subject having a cancerous tissue. The second method comprises obtaining a sample of the cancerous tissue from the subject, the sample having at least one cancer cell; measuring at least one physical parameter of the at least one cancer cell, wherein an electrical characteristic of the at least one cancer cell can be determined from the at least one physical parameter; determining a frequency of alternating electric fields to apply to the subject in order to treat the cancer based on the measured at least one physical parameter; and treating the cancer by applying an alternating electric field to the subject at the determined frequency of alternating electric fields.

In some instances of the second method, the cell membrane capacitance of the at least one cancer cell can be determined from the at least one physical parameter.

Another aspect of the invention is directed to a third method of treating cancer in a subject having a cancerous tissue. The third method comprises obtaining a sample of the cancerous tissue from the subject, the sample having at least one cancer cell; determining an electrical characteristic of the at least one cancer cell; predicting whether application of alternating electric fields to the subject would be effective to treat the cancer based on the determined electrical characteristic; and treating the cancer by applying an alternating electric field to the subject if the predicting indicates that application of alternating electric fields to the subject would be effective to treat the cancer.

In some instances of the third method, the determining of the electrical characteristic comprises measuring dielectrophoretic forces of the at least one cancer cell at each of a plurality of frequencies below 35 kHz. In some instances of the third method, the predicting is based on whether reference cancer cells that have an electrical characteristic that matches the determined electrical characteristic are susceptible to treatment using alternating electric fields. In some instances of the third method, the determining of the electrical characteristic comprises determining cell membrane capacitance.

Another aspect of the invention is directed to a fourth method of treating cancer in a subject having a cancerous tissue. The fourth method comprises obtaining a sample of the cancerous tissue from the subject, the sample having at least one cancer cell; measuring at least one physical parameter of the at least one cancer cell, wherein an electrical characteristic of the at least one cancer cell can be determined from the at least one physical parameter; predicting whether application of alternating electric fields to the subject would be effective to treat the cancer based on the measured at least one physical parameter; and treating the cancer by applying an alternating electric field to the subject if the predicting indicates that application of alternating electric fields to the subject would be effective to treat the cancer.

In some instances of the fourth method, the cell membrane capacitance of the at least one cancer cell can be determined from the at least one physical parameter.

Another aspect of the invention is directed to a fifth method of selecting a frequency of alternating electric fields to be used for treating cancer in a subject having a cancerous tissue. The fifth method comprises determining an electrical characteristic of at least one cancer cell extracted from a sample of the cancerous tissue obtained from the subject; and determining a frequency of alternating electric fields to apply to the subject in order to treat the cancer based on the determined electrical characteristic.

In some instances of the fifth method, the determining of the electrical characteristic comprises measuring dielectrophoretic forces of the at least one cancer cell at each of a plurality of frequencies below 35 kHz. In some instances of the fifth method, the determining of the frequency comprises choosing a frequency that is effective in treating reference cancer cells that have a known electrical characteristic, wherein the known electrical characteristic matches the determined electrical characteristic. In some instances of the fifth method, the determining of the electrical characteristic comprises determining cell membrane capacitance.

Another aspect of the invention is directed to a sixth method of selecting a frequency of alternating electric fields to be used for treating cancer in a subject having a cancerous tissue. The sixth method comprises measuring at least one physical parameter of at least one cancer cell extracted from a sample of the cancerous tissue obtained from the subject, wherein an electrical characteristic of the at least one cancer cell can be determined from the at least one physical parameter; and determining a frequency of alternating electric fields to apply to the subject in order to treat the cancer based on the measured at least one physical parameter.

In some instances of the sixth method, the cell membrane capacitance of the at least one cancer cell can be determined from the at least one physical parameter.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Traditionally, once a decision to use TTFields to treat a given subject was made, the frequency at which the TTFields were applied to the subject was based on the particular type of tumor that was being treated. For example, 200 kHz is the recommended frequency for TTFields when treating GBM; and 150 kHz is the recommended frequency for TTFields when treating gastric cancer. But using a single frequency for all subjects may not provide the best results in each and every one of those subjects. More specifically, while 200 kHz may be the best frequency for most subjects with GBM, certain individuals with GBM might respond better to a different frequency (e.g., 175 kHz or 225 kHz). Until now, there were no predictive markers for determining the optimal frequency that should be used for any given individual subject.

Some of the embodiments described herein can provide improved results for many subjects by customizing the frequency at which TTFields are applied to each individual subject. The decision of which frequency to use for any given individual subject is based on at least one electrical characteristic of cancer cells extracted from the individual subject. In alternative embodiments, the decision of which frequency to use for any given individual subject may be based on a physical parameter from which it is possible to determine an electrical characteristic of extracted cancer cells. The ability to predict, in advance, the best frequency at which to apply TTFields for each individual subject can advantageously improve the efficacy of TTFields treatment.

In addition, traditionally, there were no predictive markers to determine whether TTFields will be effective for any given individual subject. Some of the embodiments described herein can make a prediction of whether TTFields will be effective for a given individual subject. The prediction is based on at least one electrical characteristic of cancer cells extracted from the individual subject. In alternative embodiments, the prediction may be based on a physical parameter from which it is possible to determine an electrical characteristic of extracted cancer cells. The ability to predict, in advance, the efficacy of TTFields treatment for any given subject can advantageously improve outcomes (e.g., by selecting the most effective treatment for each individual subject).

Examples of electrical characteristics that can be used to make these predictions include but are not limited to dielectrophoretic force, cell membrane capacitance, cell membrane resistance, cytoplasm conductivity, as well as other measures of permittivity, conductivity, capacitance, etc. of various cellular structures. The electrical characteristic that is used to make the predictions may be measured directly. Alternatively, the electrical characteristic may be measured indirectly (e.g., by measuring an other physical characteristic, which could be either a different electrical characteristic or a non-electrical characteristics such as light intensity) and determining the electrical characteristic from the other physical characteristic. In situations where an electrical characteristic can be determined from an other physical characteristic, it may be possible to make a mapping from the other physical characteristic directly to the desired TTFields frequency (or the effectiveness prediction) without making an intermediate calculation of the relevant electrical characteristic, as explained in more detail below.

In some embodiments, the electrical characteristic that is used to make the predictions noted above is the dielectrophoretic force on the cancer cells. Any of a variety of commercially available systems for measuring the dielectrophoretic force may be used, including but not limited to the 3DEP™ 3D Dielectrophoresis Cell Analysis System. (Dielectrophoresis is a physical effect that generates a force on polarizable particles experiencing a non-homogeneous electric field and can therefore be used as a technique to analyze the way cells move within electric fields at different frequencies.) Note that in place of determining the electrical characteristic by measuring the dielectrophoretic force on the cancer cells (as in the 3DEP™ system), a variety of alternative approaches for determining an electrical characteristic of the cancer cells that will be apparent to persons skilled in the relevant art may also be used.

First Set of Embodiments: Determining a Frequency at which TTFields Treatment should be Applied Based on the Cancer Cells' Electrical Properties To establish how a measured electrical characteristic can be used to determine the frequency of TTFields that should be applied to a subject in order to treat the subject's cancer, the baseline electrical properties (permittivity and conductivity) of 18 cell lines from different tumor types were determined using a 3DEP™ Cell Analysis System. Of those 18 cell lines, it was first established that 10 of those cell lines (HepG2, A549, H1299, MDA231, LLC-1, C3A, AGS, KATO III, H2052, and RN5) were most vulnerable to treatment using TTFields at a frequency of 150 kHz; and 8 of those cell lines (A172, A2780, U87, A375, LN18, LN229, DKMG, and U251) were most vulnerable to treatment using TTFields at a frequency of 200 kHz. The optimal TTFields frequency for all 18 cell lines was determined by testing the cytotoxic effect of TTFields at various frequencies, using the Inovitro™ system.

Figure 1:
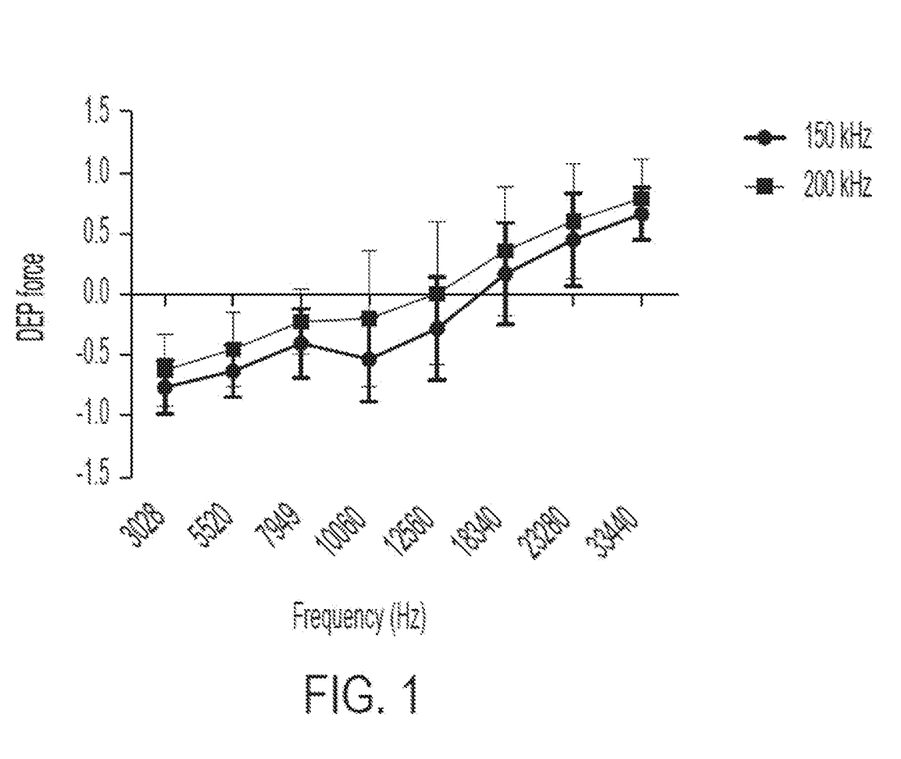
FIG. 1 depicts variations in dielectrophoretic forces between two groups of cell lines for which the optimal TTFields frequency is 150 kHz and 200 kHz, respectively.

The electrical properties of each of the cell lines were then compared with the optimal TTFields frequency and sensitivity of each cell line. The results of this comparison are depicted in FIG. 1, which demonstrates the differences of the lower frequency range (3-35 kHz) of the dielectrophoretic force vs. frequency curves of cells between the first group of 10 cell lines (for which the optimal TTFields frequency is 150 kHz) and the second group of 8 cell lines (for which the optimal TTFields frequency is 200 kHz).

The curves were analyzed using 2-way ANOVA. A comparison of the dielectrophoretic force of the first group of cell lines with the dielectrophoretic force of the second group of cell lines reveals that there was a significant difference between the dielectrophoretic force of those two groups at the lower frequency range of the dielectrophoretic force vs. frequency curves. More specifically, these results demonstrate significant differences ($p<0.001$) between the lower frequency range of the dielectrophoretic force vs. frequency curves as between the first and second groups of cell lines. Based on the differences in the curves in this low frequency range, the inventors have concluded that the electrical characteristic of dielectrophoretic force in this low frequency range is a good predictor for the optimal frequency for TTFields treatment.

Figure 2:
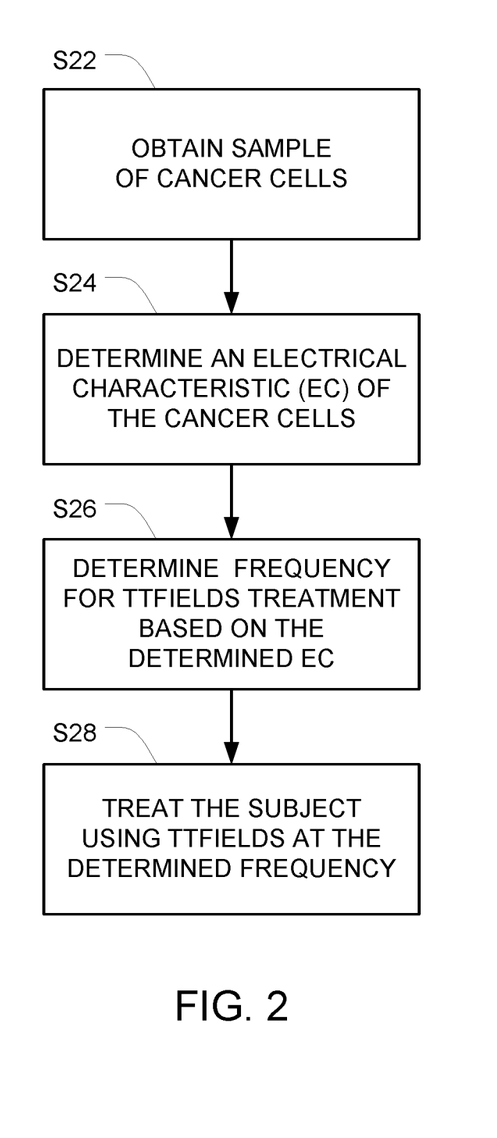
FIG. 2 depicts a process for selecting a frequency for TTFields treatment based on dielectrophoretic force measurements.

FIG. 2 depicts a process that takes advantage of this difference. In step S22, tumor cells are extracted from a subject (e.g., taken from resection/biopsy/circulating tumor cells). Then, in step S24, the electrical characteristics of the cancer cells are determined. One way to do this is to dissociate the extracted tumor cells into single cells suspensions (using a method such as a tumor dissociation kit). The electrical properties of the cells in the single cell suspension could either be tested directly using a device which measures the electrical properties (e.g. using a 3DEP™ device to measure dielectrophoretic forces) or could be further purified to create a more homogenous cell population by sorting out other infiltrating cells, using a method such as Fluorescence-activated cell sorting (FACS) or using cell specific beads and then measuring the electrical properties by a device such as 3DEP™.

After the electrical characteristic of the at least one cancer cell from the subject is determined, the frequency of TTFields that should be applied to the subject in order to treat the subject's cancer can be determined based on the determined electrical characteristic in step S26. For example, in a situation where the electrical characteristic being analyzed is dielectric force, if the dielectric force measurements on the tumor cells from the subject more closely matches the dielectric forces for the first group of cell lines, treatment for that subject should proceed using TTFields at a frequency of 150 kHz. On the other hand, if the dielectric force measurements on the tumor cells from the subject more closely matches the second group of cell lines, treatment for that subject should proceed using TTFields at a frequency of 200 kHz.

After the frequency for TTFields treatment has been determined, the cancer is treated by applying TTFields to the subject at the determined frequency in step S28.

Because the lower frequency range of the dielectrophoretic force vs. frequency curves corresponds to membrane capacitance of cells, the cell membrane capacitance can be determined from dielectrophoretic force vs. frequency data (such as the data depicted in FIG. 1). Thus, the inventors have concluded that the electrical characteristic of cell membrane capacitance is also a good predictor for the optimal frequency for TTFields treatment. In a situation where cell membrane capacitance is calculated based on dielectrophoretic force measurements, using cell membrane capacitance as a predictor for the optimal frequency for TTFields treatment is an example of indirectly determining a second electrical characteristic (i.e., cell membrane capacitance) based on a first electrical characteristic (i.e., dielectrophoretic force), and then using the second electrical characteristic as a predictor for the optimal frequency for TTFields treatment.

The process depicted in FIG. 2 also applies to the situation where cell membrane capacitance is used as the electrical characteristic. In this situation, tumor cells are extracted from a subject in step S22 (e.g., as described above). Then, in step S24, the cell membrane capacitance of the cancer cells is determined. This may be accomplished, for example, using a 3DEP™ device to measure dielectrophoretic forces, and then determining the cell membrane capacitance based on the measured dielectrophoretic forces. A mapping between cell membrane capacitance and the optimal TTFields frequency is then made in step S26. For example, if the cell membrane capacitance of the tumor cells from the subject more closely matches the cell membrane capacitance for the first group of cell lines, treatment for that subject should proceed using TTFields at a frequency of 150 kHz. On the other hand, if the cell membrane capacitance of the tumor cells from the subject more closely matches the second group of cell lines, treatment for that subject should proceed using TTFields at a frequency of 200 kHz. The cancer is then treated by applying TTFields to the subject at the determined frequency in step S28.

As described above, dielectrophoretic force data can be used to predict the optimal frequency for TTFields treatment. One way to measure dielectrophoretic force (which is used in the 3DEP™ system) is to first make optical measurements to determine how far extracted cancer cells move in an electric field, then convert those optical measurements into dielectrophoretic force data (which is an electrical characteristic), and then map the dielectrophoretic force data to the optimal frequency. It is therefore possible to omit the converting step, and to make a direct mapping from the underlying optical measurements to the optimal frequency for TTFields treatment. This is an example of measuring a physical (i.e., optical) parameter of extracted cancer cells, where an electrical characteristic (i.e., dielectrophoretic force) of the cancer cells can be determined from the physical parameter, and then determining the TTFields frequency based on the physical parameter (even though the dielectrophoretic force value was never actually determined).

Figure 3:
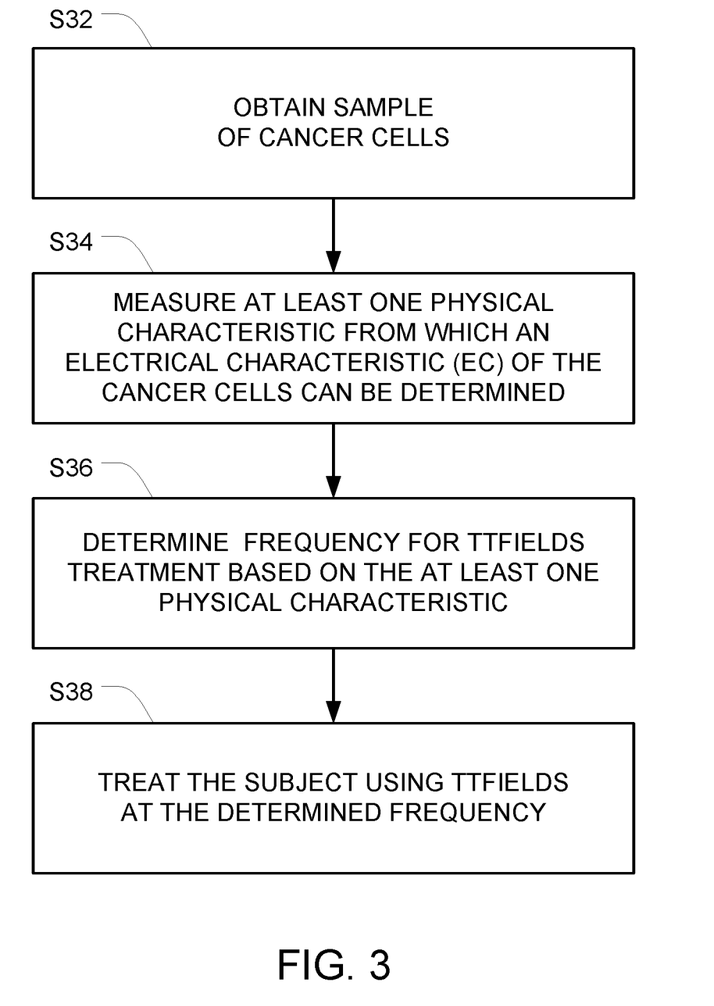
FIG. 3 depicts a process for selecting a frequency for TTFields treatment based on optical measurements, when it is possible to determine an electrical characteristic (e.g., dielectrophoretic force or cell membrane capacitance) from the optical measurements.

The process depicted in FIG. 3 applies in this situation. Here, tumor cells are extracted from a subject in step S32 (e.g., as described above in connection with step S22). Then, in step S34, physical characteristics of the cancer cells (e.g., movement within a well in the 3DEP™ system as determined by measuring light intensity) are determined. A mapping between the measured light intensity and the optimal TTFields frequency is then made in step S36. For example, if the light intensity measured for the tumor cells from the subject more closely matches the light intensity measured for the first group of cell lines, treatment for that subject should proceed using TTFields at a frequency of 150 kHz. On the other hand, if the light intensity measured for tumor cells from the subject more closely matches the light intensity measured for the second group of cell lines, treatment for that subject should proceed using TTFields at a frequency of 200 kHz. The cancer is then treated by applying TTFields to the subject at the determined frequency in step S38.

Second Set of Embodiments: Prediction of Cancer Cells' Response to TTFields Treatment Based on the Cancer Cells' Electrical Properties In other embodiments, a prediction can be made as to whether TTFields treatment will be effective for any given individual subject based on an electrical characteristic of cancer cells in the body of the given individual subject. The electrical characteristic of the cancer cells from the given individual subject may be determined using any of the approaches (e.g., 3DEP™) described above in connection with the frequency-selecting embodiment.

To establish how this prediction can be made, 3DEP™ measurements were made on a first group of 7 distinct cell lines that were known to experience high cytotoxicity when TTFields were applied to those cell lines (LN18, LN229, A375, A2780, MDA231, LLC-1, and AGS), and on a second group of 6 distinct cell lines that were known to experience low cytotoxicity when TTFields were applied to those cell lines (MCF7, U251, DKMG, KATO III, CT26, and RN5). The cytotoxic effect of TTFields on the various cell lines was determined using the Inovitro™ system.

Figure 4:
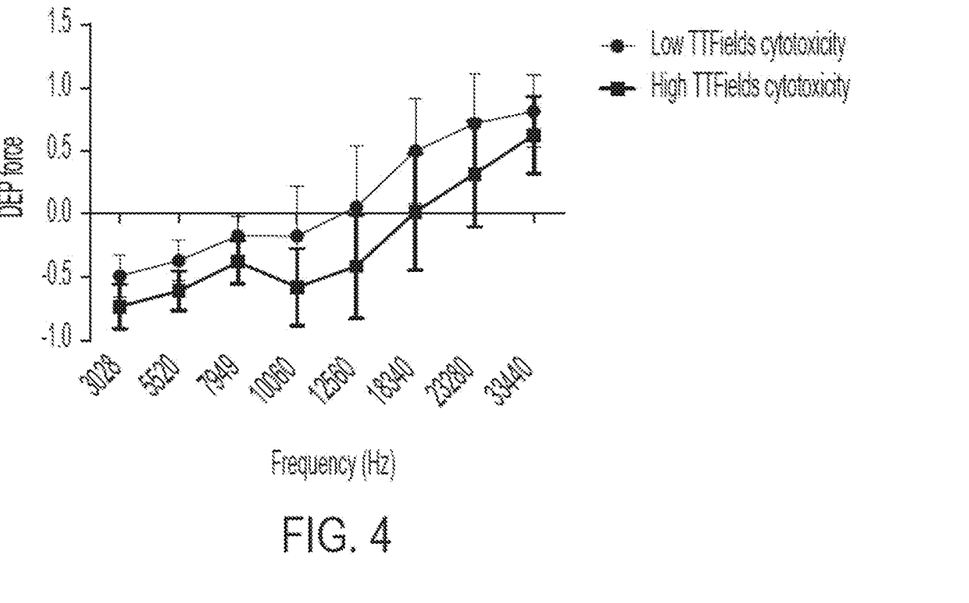
FIG. 4 depicts variations in dielectrophoretic forces between two groups of cell lines, one of which is sensitive to TTFields and one of which is not sensitive to TTFields.

The electrical properties of these two groups of cell lines were then compared. The results of this comparison are depicted in FIG. 4, which demonstrates the differences of the lower frequency range (3-35 kHz) of the dielectrophoretic force vs. frequency curves of cells between the first group of cell lines and the second group of cell lines. And as noted above, this lower range of these curves corresponds to membrane capacitance.

This distinction can be used to help decide whether a given subject should be treated with TTFields, not treated, or treated using TTFields in combination with another modality.

These results demonstrate significant differences (2-way ANOVA $p<0.001$) between the lower frequency range of the dielectrophoretic force vs. frequency curves (which corresponds to membrane capacitance of cells) as between the first and second groups of cell lines. Based on the differences in the curves in this low frequency range, the inventors have concluded that the electrical characteristic of dielectrophoretic force in this low frequency range is a good predictor as to whether a given set of cancer cells will respond well to TTFields treatment.

Figure 5:
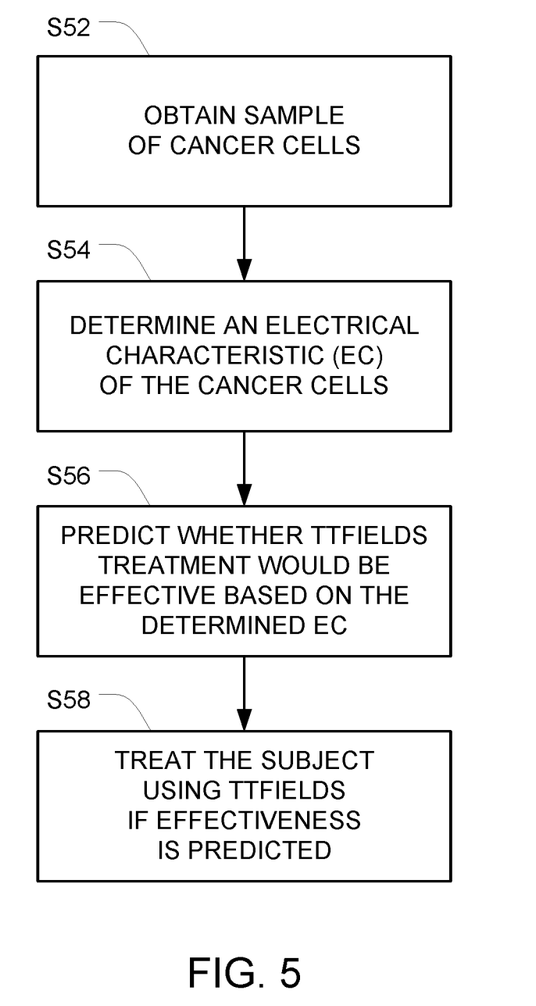
FIG. 5 depicts a process for determining whether to treat a particular subject with TTFields based on dielectrophoretic force measurements.

FIG. 5 depicts a process that takes advantage of this difference. In step S52, tumor cells are extracted from a subject (e.g., taken from resection/biopsy/circulating tumor cells). Then, in step S54, the electrical characteristics of the cancer cells are determined (e.g., as described above in connection with step S24).

After the electrical characteristic of the at least one cancer cell from the subject is determined, a prediction is made as to whether application of TTFields to the subject would be effective to treat the cancer based on the determined electrical characteristic in step S56. For example, in a situation where the electrical characteristic being analyzed is dielectric force, if the dielectric force measurements on the tumor cells from the subject more closely matches the first group of cell lines (that were known to experience high cytotoxicity when TTFields were applied), treatment for that subject using TTFields has a high probability of effectiveness. On the other hand, if the dielectric force measurements on the tumor cells from the subject more closely matches the second group of cell lines, the probability of effectiveness using TTFields is low, and treatment for that subject should proceed using an alternative approach.

Finally, if the results of the prediction in step S56 reveal that treatment using TTFields has a high probability of effectiveness, the cancer is treated in step S58 by applying TTFields to the subject at an appropriate frequency.

Because the lower frequency range of the dielectrophoretic force vs. frequency curves corresponds to membrane capacitance of cells, the cell membrane capacitance can be determined from dielectrophoretic force vs. frequency data (such as the data depicted in FIG. 4). Thus, the inventors have concluded that the electrical characteristic of cell membrane capacitance is also a good predictor for the effectiveness of TTFields treatment. In a situation where cell membrane capacitance is calculated based on dielectrophoretic force measurements, using cell membrane capacitance as a predictor for the effectiveness of TTFields treatment is an example of indirectly determining a second electrical characteristic (i.e., cell membrane capacitance) based on a first electrical characteristic (i.e., dielectrophoretic force), and then using the second electrical characteristic as a predictor for the effectiveness of TTFields treatment.

The process depicted in FIG. 5 also applies to the situation where cell membrane capacitance is used as the electrical characteristic. In this situation, tumor cells are extracted from a subject in step S52 (e.g., as described above in connection with step S22). Then, in step S54, the cell membrane capacitance of the cancer cells is determined (e.g., as described above in connection with step S24). Next, in step S56, a prediction of whether TTFields treatment would be effective is made based on the determined cell membrane capacitance. For example, if the cell membrane capacitance of the tumor cells from the subject more closely matches the cell membrane capacitance for the first group of cell lines (that were known to experience high cytotoxicity when TTFields were applied), treatment for that subject using TTFields has a high probability of effectiveness. On the other hand, if the cell membrane capacitance of the tumor cells from the subject more closely matches the second group of cell lines, the probability of effectiveness using TTFields is low, and treatment for that subject should proceed using an alternative approach. Finally, if the results of the prediction in step S56 reveal that treatment using TTFields has a high probability of effectiveness, the cancer is treated in step S58 by applying TTFields to the subject at an appropriate frequency.

Because (a) dielectrophoretic force data can be used to predict whether TTFields treatment will be effective (as described above in connection with FIG. 4-5); and (b) optical measurements can be converted into dielectrophoretic force data (as described above in connection with FIG. 3), it is possible to make a prediction directly from the underlying optical measurements as to whether treatment with TTFields will be effective for a particular subject without ever making the intermediate step of determining the dielectrophoretic force data. This is an example of measuring a physical (i.e., optical) parameter of extracted cancer cells, wherein an electrical characteristic (i.e., dielectrophoretic force) of the cancer cells can be determined from the physical parameter, and then predicting whether applying TTFields would be effective to treat the subject's cancer based on the physical parameter (even though the dielectrophoretic force value was never actually determined).

Figure 6:
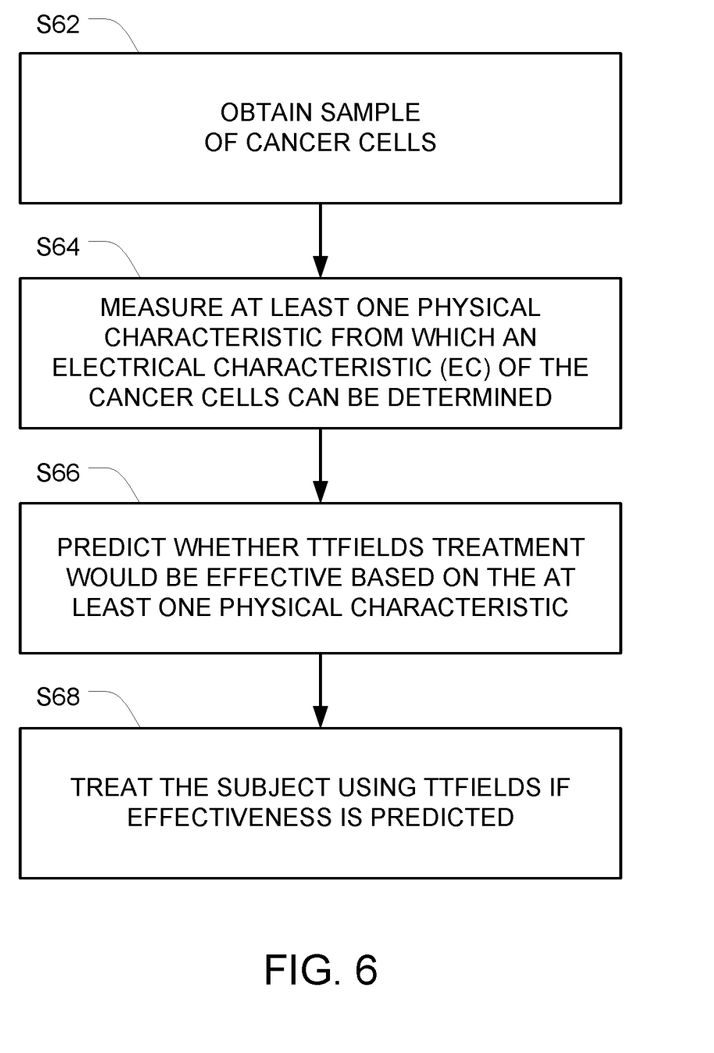
FIG. 6 depicts a process for determining whether to treat a particular subject with TTFields based on optical measurements, when it is possible to determine an electrical characteristic (e.g., dielectrophoretic force or cell membrane capacitance) from the optical measurements.

The process depicted in FIG. 6 applies in this situation. Here, tumor cells are extracted from a subject in step S62 (e.g., as described above in connection with step S22). Then, in step S64, physical characteristics of the cancer cells (e.g., movement within a well in the 3DEP™ system as determined by measuring light intensity) are determined. A mapping between the measured light intensity and the prediction as to whether TTFields treatment will be effective is then made in step S66. For example, if the measured light intensity for the tumor cells from the subject more closely matches the first group of cell lines (that were known to experience high cytotoxicity when TTFields were applied), treatment for that subject using TTFields has a high probability of effectiveness. On the other hand, if the light intensity for the tumor cells from the subject more closely matches the second group of cell lines, the probability of effectiveness using TTFields is low, and treatment for that subject should proceed using an alternative approach. Finally, if the results of the prediction in step S66 reveal that treatment using TTFields has a high probability of effectiveness, the cancer is treated in step S68 by applying TTFields to the subject at an appropriate frequency.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating cancer in a subject, the method comprising:
   extracting at least one cancer cell from the subject's body;
   determining an electrical characteristic of the extracted at least one cancer cell;
   determining a frequency of alternating electric fields to apply to the subject in order to treat the cancer based on the determined electrical characteristic; and
   treating the cancer by applying an alternating electric field to the subject at the determined frequency of alternating electric fields.

2. The method of claim 1, wherein the determining of the electrical characteristic comprises measuring dielectrophoretic forces of the extracted at least one cancer cell at each of a plurality of frequencies below 35 kHz.

3. The method of claim 1, wherein the determining of the frequency comprises choosing a frequency that is effective in treating reference cancer cells that have a known electrical characteristic, wherein the known electrical characteristic matches the determined electrical characteristic.

4. The method of claim 1, wherein the determining of the electrical characteristic comprises determining cell membrane capacitance.

5. A method of treating cancer in a subject, the method comprising:
   extracting at least one cancer cell from the subject's body;
   measuring dielectrophoretic force of the extracted at least one cancer cell;
   determining a frequency of alternating electric fields to apply to the subject in order to treat the cancer based on the measured dielectrophoretic force; and
   treating the cancer by applying an alternating electric field to the subject at the determined frequency of alternating electric fields.

6. The method of claim 5, wherein the cell membrane capacitance of the at least one cancer cell can be determined from the measured dielectrophoretic force.

7. A method of treating cancer in a subject, the method comprising:
   extracting at least one cancer cell from the subject's body;
   determining an electrical characteristic of the extracted at least one cancer cell;
   predicting whether application of alternating electric fields to the subject would be effective to treat the cancer based on the determined electrical characteristic; and
   treating the cancer by applying an alternating electric field to the subject if the predicting indicates that application of alternating electric fields to the subject would be effective to treat the cancer.

8. The method of claim 7, wherein the determining of the electrical characteristic comprises measuring dielectrophoretic forces of the extracted at least one cancer cell at each of a plurality of frequencies below 35 kHz.

9. The method of claim 7, wherein the predicting is based on whether reference cancer cells that have an electrical characteristic that matches the determined electrical characteristic are susceptible to treatment using alternating electric fields.

10. The method of claim 7, wherein the determining of the electrical characteristic comprises determining cell membrane capacitance.

11. A method of treating cancer in a subject the method comprising:
    extracting at least one cancer cell from the subject's body;
    measuring dielectrophoretic force of the extracted at least one cancer cell;
    predicting whether application of alternating electric fields to the subject would be effective to treat the cancer based on the measured dielectrophoretic force; and
    treating the cancer by applying an alternating electric field to the subject if the predicting indicates that application of alternating electric fields to the subject would be effective to treat the cancer.

12. The method of claim 11, wherein the cell membrane capacitance of the at least one cancer cell can be determined from the measured dielectrophoretic force.

* * * * *